(12) United States Patent  (10) Patent No.: US 8,529,940 B2
Sunvold et al.  (45) Date of Patent: Sep. 10, 2013

(54) DIETARY METHOD FOR MODULATING GLUCOSE METABOLISM

(75) Inventors: Gregory Dean Sunvold, Lewisburg, OH (US); Michael Anthony Ceddia, Brookville, OH (US); Jacqueline Sinclair Rand, Brisbane (AU)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/362,374

(22) Filed: Jan. 31, 2012

(65) Prior Publication Data

US 2012/0164265 A1   Jun. 28, 2012

Related U.S. Application Data

(62) Division of application No. 10/442,521, filed on May 21, 2003, now Pat. No. 8,142,810.

(60) Provisional application No. 60/384,320, filed on May 30, 2002.

(51) Int. Cl.
*A23K 1/00* (2006.01)

(52) U.S. Cl.
USPC .......................................................... 424/442

(58) Field of Classification Search
None
See application file for complete search history.

(56) References Cited

U.S. PATENT DOCUMENTS

| | | | |
|---|---|---|---|
| 5,776,887 A * | 7/1998 | Wibert et al. | 514/5.5 |
| 5,932,258 A | 8/1999 | Sunvold et al. | |
| 6,071,544 A | 6/2000 | Sunvold et al. | |
| 6,203,825 B1 * | 3/2001 | Hodgkins | 426/2 |

FOREIGN PATENT DOCUMENTS

| | | |
|---|---|---|
| DE | 29 47 503 A1 | 5/1981 |
| EP | 0362396 | 4/1990 |
| WO | WO 02/05782 A1 | 7/2002 |

OTHER PUBLICATIONS

Health 410, Optimal Nutrition for Exercise and Good health, 2000.*
Butchi, Lakshmi K. et al., "Hypoglycemic Effect of Selected Sorghum Recipes," Nutrition Research, Elsevier, Inc, XX, vol. 16, No. 10, Jan. 1, 1996.
Foster-Powell, K. et al., "International Table of Glycemic Index and Glycemic Load Values: 2002," The American Journal of Clinical Nutrition, American Society for Nutrition, US, vol. 76, No. 1, Jul. 1, 2002.
Decision to Refuse a European Patent application, Application No. 03 756 266.7-2114, mailed Aug. 4, 2011, 9 pages.
Martin, L. et al., "Rocommendations Nutritionnelles dans le Traitement des Principales Affections Due Chat", LePoint Veterinaire, vol. 28, No. 178, Aug. 1996, pp. 1996-2008.
Jones, B. R. et al., "Cutaneous Xanthomata Associated with diabetes Mellitus in a Cat", Journal of Small Animal Practice, Blackwell Scientific Publications, Oxford, GB, vol. 26, No. 1, 1985, pp. 33-42.

(Continued)

*Primary Examiner* — Anand Desai
*Assistant Examiner* — Melissa Mercier
(74) *Attorney, Agent, or Firm* — Adam W. Borgman; Amy M. Foust

(57) ABSTRACT

The invention provides a method for treating abnormal glucose metabolism and insulin resistance in an animal by feeding a diet comprising high protein and moderate amounts of carbohydrate and fat. The invention also provides a method for treating conditions associated with insulin resistance or decreased longevity by feeding an animal such diets.

17 Claims, 9 Drawing Sheets

(56) References Cited

OTHER PUBLICATIONS

Romsos, D. R. et al., "Effects of Dietary Carbohydrate, Fat and Protein on Growth, Body Compostion and Blood Metabolite Levels in the Dog", Journal of Nutrition, Wistar Institute of Anatomy and Biology, Philadelphia, PA, U.S., vol. 106, No. 10, 1978, pp. 1452-1464.

Baba, N. Hwalla et al., "High Protein vs. High Carbohydrate Hypoenergetic Diet for the Treatment of Obese Hyperinulinemic Subjects", International Journal of Obesity, vol. 23, No. 11, Nov. 1999, pp. 12302-1206.

St. Jeor Sachiko, T. et al., "Dietary, Protein and Weight Reduction—A Statement for Healthcare Professionals form the Nutrition Committee of the Council on Nutrition, Physical Activity, and Metabolism of the American Heart Association", Circulation, vol. 104, No. 15, Oct. 9, 2001, pp. 1869-1874.

* cited by examiner

DIETARY METHOD FOR MODULATING GLUCOSE METABOLISM

CROSS REFERENCE TO RELATED APPLICATION

This application is a divisional of U.S. patent application Ser. No. 10/442,521, filed May 21, 2003, now U.S. Pat. No. 8,142,810, which claims the benefit of U.S. Provisional Application No. 60/384,320, filed May 30, 2002, each of which is hereby incorporated by reference in its entirety.

FIELD OF THE INVENTION

The present invention relates to methods for treating abnormal conditions associated with glucose metabolism. The invention also relates to methods for increasing longevity, particularly by modulating glucose metabolism and decreasing the development of insulin resistance.

BACKGROUND OF THE INVENTION

Companion animals are known to suffer from many of the same health conditions as humans. Therefore, it is not uncommon for prevention and treatment methods for dogs and cats to closely follow those for humans. For example, diabetes is one of the most frequently diagnosed endocrinopathies of cats and treatment of diabetes in cats is similar to treatment of diabetes in humans. Human therapies such as insulin therapy, oral hypoglycemics, and dietary modulation of glucose metabolism and weight loss are commonly used in both domestic felines and canines.

Human diets have traditionally been high in carbohydrates, and diets for companion animals, especially cats, have also been high in carbohydrates. In recent years, however, studies have suggested that high carbohydrate intake may be correlated with abnormal glucose metabolism and disease states associated with abnormal glucose metabolism. In response to these studies, diets have been formulated to decrease carbohydrate intake in the hope that decreasing carbohydrate intake will provide a healthier diet and more effectively manage glucose metabolism or its associated disease states.

For humans, the well-known Atkins' diet promotes the use of higher amounts of protein and fat in the diet in order to offset the decreased intake of carbohydrates, resulting in a significantly reduced percentage of caloric intake from carbohydrates even though the diet does not require decreased overall intake of calories. For companion animals, diets such as those described in U.S. Pat. No. 6,203,825, and those provided commercially as Purina DM Diabetes Management Feline Formula (Nestle Purina Pet Care Company), also limit the percentage of calories derived from carbohydrate sources, This type of diet, as described generally in the examples included in U.S. Pat. No. 6,203,825 as Diets 1 through 3, provides a high percentage of calories in the form of dietary fat (Diet 1 (55%), Diet 2 (48%) and Diet 3 (61%), The high percentage of calories from dietary fat puts the animal at risk for unwanted weight gain. This is an indirect side effect of limiting the amount of calories from carbohydrates.

The effect of high fat diets on glucose and insulin concentrations in companion. animals has not been characterized. However, there is evidence from human studies that high fat diets may contribute to insulin resistance and lipotoxicity of beta cells, and studies performed in rats have demonstrated that high fat levels in the diet induce insulin resistance in muscle (Youngren el al., "Impaired insulin-receptor autophosphorylation is an early defect in fat-fed, insulin-resistant rats," *J. Appl. Physiol*, Vol. 91, p. 2240 (2001)), Furthermore, long-chain free fatty acids are known to interfere, with insulin-mediated glucose metabolism, and increased tissue triglycerides have been correlated with development of insulin resistance (Koyama et al., "Tissue triglycerides, insulin resistance, and insulin production: implications for hyperinsulinemia of obesity," *Am. J. Physiol.*, Vol. 273, E708 (1997)).

Diet restriction has also been described to have a benefit to humans, as well as other animals, by lowering insulin levels and insulin resistance (Reaven et al., "Effect of age and diet on insulin secretion and insulin action in the rat," *Diabetes*, Vol. 32, 175 (1983)) and increasing life span and age-associated changes (Kealy et al., "Effects of diet restriction on life span and age-related changes in dogs," *JAVMA*, Vol. 220, 1315 (2002)).

For many individuals, both personally and as pet owners, it may be difficult to restrict caloric intake to the necessary levels, no matter how positive the effects might be. Additionally, excessive fat intake can be associated with excess weight gain. Therefore, the need still exists for a dietary method for treating the development of abnormal glucose metabolism and associated conditions (e.g., insulin resistance) or increasing longevity.

SUMMARY OF THE INVENTION

The present invention relates to various methods for the treatment of humans and other animals, particularly companion animals (e.g., domestic felines, canines, horses, cows, and the like). In one embodiment, the present invention relates to a method for treating diseases of abnormal glucose metabolism, or associated conditions, by providing a diet formulation comprising moderate amounts of carbohydrate and fat in combination with higher amounts of protein.

In yet another embodiment, the present invention further relates to a method for decreasing abnormalities of glucose metabolism that are associated with decreased longevity, thereby increasing longevity. The method provides a diet formulation comprising higher amounts of protein, in conjunction with moderate mounts of fat and carbohydrate.

In one embodiment, the diet comprises, on a dry matter weight basis, protein at a level of at least about 40%, carbohydrate at a level of equal to or less than about 32%, and fat at a level of equal to or less than about 17%. Alternatively or additionally, the diet comprises, on a percent of calories basis, protein at a level of at least about 40%, carbohydrate at a level of equal to or less than about 35%, and fat at a level of equal to or less than about 32%. These levels are particularly useful for companion animal diets. Other representative diets are described herein.

DETAILED DESCRIPTION OF THE INVENTION

Figure 1:
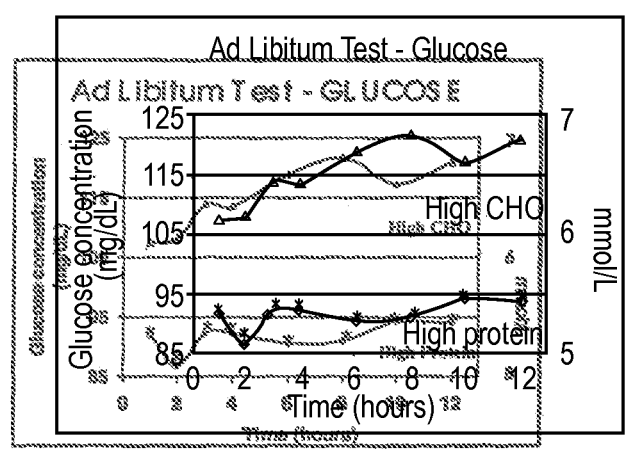
FIG. 1 is a graph illustrating the plasma glucose concentrations (expressed as mg/dL) measured in fluid samples taken from cats following the ad libitum feeding test described under "Examples" in this specification. Glucose concentrations are shown on the Y axis and time at which the blood sample was taken is shown on the X axis. Results are shown contrasting Diet 1 with Diet 3 (high protein, high carbohydrate, respectively).
Figure 2:
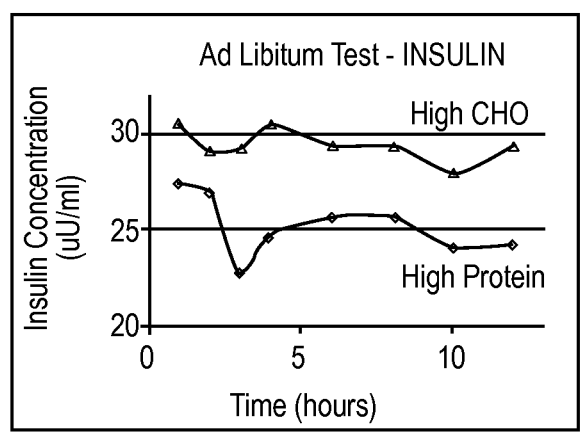
FIG. 2 is a graph illustrating the plasma insulin concentrations (expressed as uU/ml) measured in blood samples taken from cats following the ad libitum feeding test. Insulin concentration is indicated on the Y axis and time at which the blood sample was taken in shown on the X axis. Results are shown contrasting Diet 1 (high protein) with Diet 3 (high carbohydrate).
Figure 3:
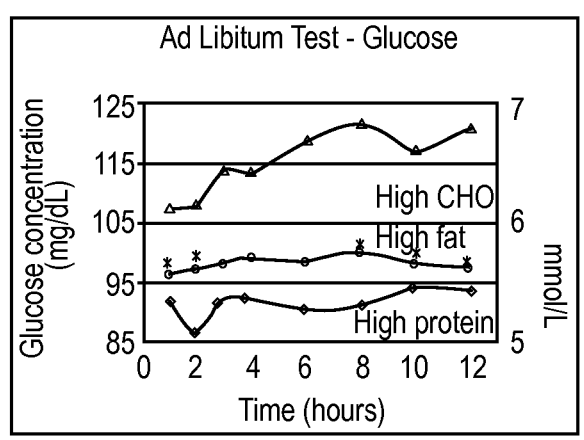
FIG. 3 is a graph illustrating the plasma glucose concentration (expressed as mg/dL) measured in blood samples taken from cats following the ad libitum feeding test. Glucose concentrations are shown on the Y axis and time at which the blood sample was taken is shown on the X axis. Results are shown contrasting glucose concentrations in cats following feeding of Diet 1, Diet 2, and Diet 3, with Diet 2 being a higher fat diet.
Figure 4:
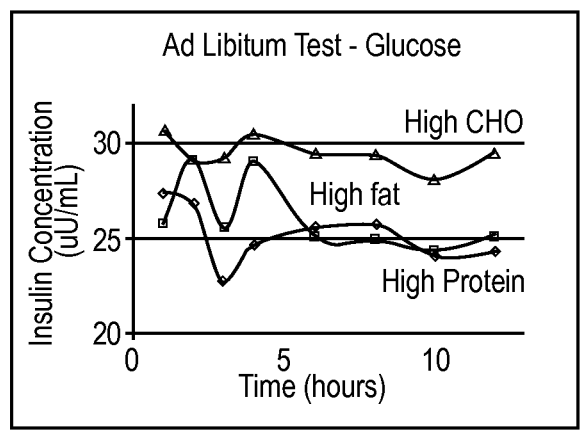
FIG. 4 is a graph illustrating the plasma insulin concentrations (expressed as uU//ml) measured in blood samples taken from cats following the ad libitum feeding test. Insulin concentration is indicated on the Y axis and time at which the blood sample was taken in shown on the X axis. Results are shown contrasting Diet 1 (high protein), Diet 2 (high fat), and Diet 3 (high carbohydrate).
Figure 5:
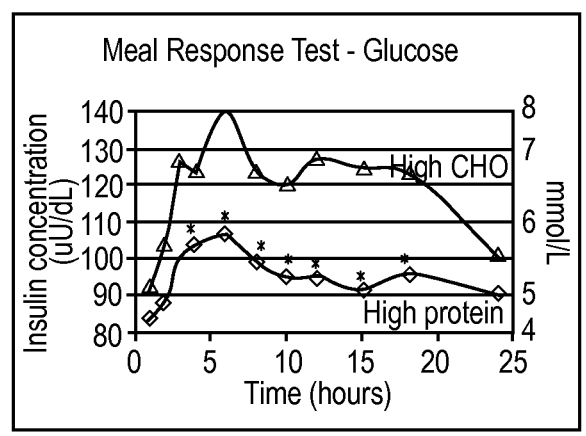
FIG. 5 is a graph illustrating the plasma glucose concentrations (expressed as mg/dL) measured in blood samples taken from cats following the meal response feeding test described under "Examples" in this specification. Glucose concentrations are shown on the Y axis and time at which the blood sample was taken is shown on the X axis. Results are shown contrasting Diet 1 with Diet 3 (high protein, high carbohydrate, respectively).
Figure 6:
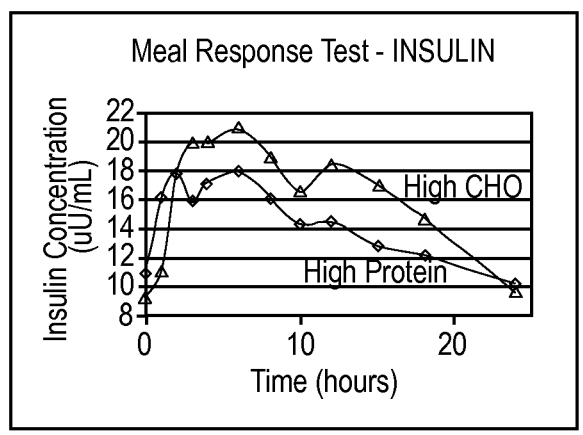
FIG. 6 is a graph illustrating the plasma insulin concentrations (expressed as uU/ml) measured in blood samples taken from cats following the meal response feeding test. Insulin concentration is indicated on the Y axis and time at which the blood sample was taken in shown on the X axis. Results are shown contrasting Diet 1 (high protein) with Diet 3 (high carbohydrate).
Figure 7:
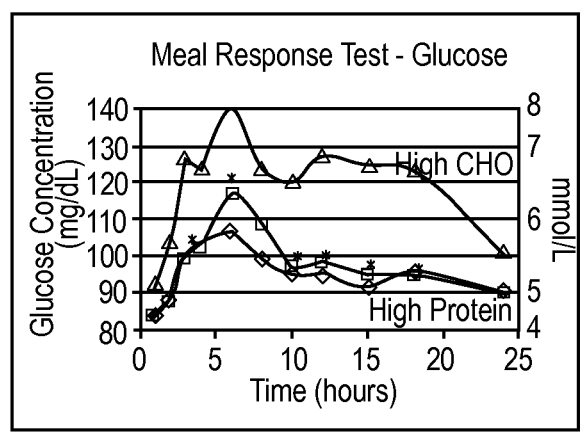
FIG. 7 is a graph illustrating the plasma glucose concentration (expressed as mg/dL) measured in blood samples taken from cats following the meal response feeding test. Glucose concentrations are shown on the Y axis and time at which the blood sample was taken is shown on the X axis, Results are shown contrasting glucose concentrations in cats following feeding of Diet 1, Diet 2, and Diet 3, with Diet 2 being a higher fat diet.
Figure 8:
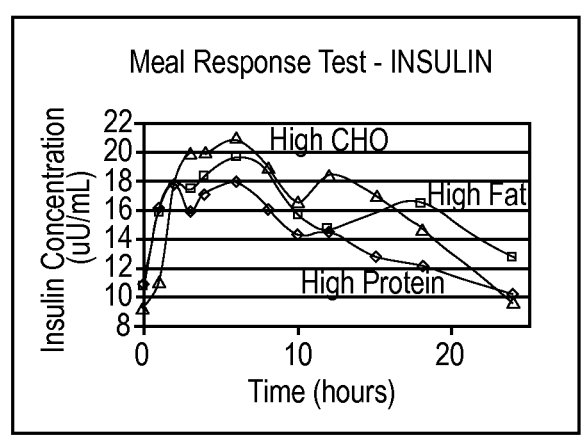
FIG. 8 is a graph illustrating the plasma insulin concentrations (expressed as uU/mL) measured in blood samples taken from cats following the meal response feeding test. insulin concentration is indicated on the Y axis and time at which the blood sample was taken in shown on the X axis. Results are shown contrasting Diet 1 (high protein), Diet 2 (high fat), and Diet 3 (high carbohydrate).

The inventors have discovered that feeding low carbohydrate/high fat diets designed for management of glucose levels in animals with diabetes can result in a greater insulin: glucose ratio, which is an indicator of decreased sensitivity to insulin and associated development of insulin resistance (see, for example, Legro et al., "A fasting glucose to insulin ratio is a useful measure of insulin sensitivity in women with polycystic ovary syndrome," *J. Clin. Endocrinology and Metabolism*, Vol. 83, 2694, 1998). The inventors have also discovered that, contrary to prior theories regarding management of glucose metabolism, high protein diets with moderate carbohydrate and fat, rather than high fat diets with low carbohydrate, provide lower postprandial glucose and insulin ratios associated with the prevention of insulin resistance.

In the method described by the present invention, glucose management is therefore accomplished by providing a diet that is high in protein, while containing moderate amounts of carbohydrate and lower amounts of fat. This method is utilized for humans and other animals, particularly companion animals such as domestic canines and felines. Treatment of these companion animals is particularly preferred. As such, the method of the present invention is useful for the treatment of abnormal glucose metabolism, or conditions associated therewith such as insulin resistance, diabetes, pre-diabetes (sometimes characterized in the art as Syndrome X), hypertriglyceridemia, hyperlipidemia, and combinations thereof. As used herein, the term "treatment" includes prevention of, inhibition of, and modulation of, the symptoms or presence of the referenced condition. The present method is alternatively or additionally useful for the enhancement of longevity in an animal, particularly through modulation of abnormal glucose metabolism.

The method of the invention is enabled through administration of a diet formulation to an animal, wherein the diet formulation comprises moderate amounts of carbohydrate and fat in combination with higher amounts of protein. The animal may be a human or other animal, and is preferably a companion animal such as a domestic canine or feline. Frequency of administration is not limited. However, the diets are typically administered on an infrequent or as-needed basis or are preferably administered in a more routine manner once, twice, or three times daily. To illustrate, for companion animals, the diet can be provided ad libitum or, for added health benefit, as measured portions using feeding guidelines known to those of skill in the art, As used herein, the term "administration" (or the like) with regard to a particular diet formulation means to provide the composition to an animal (including oneself or another animal) and/or to direct, instruct, or advise the use of the diet formulation for a purpose described herein. Wherein the administration of the diet is directed, instructed or advised, such direction may be that which instructs and/or informs the user (including, for example, the owner in the case of companion animals), that use of the composition may and/or will provide one or more of the benefits described herein.

Administration which is directed may comprise, for example, oral direction (e.g., through oral instruction from, for example, a physician, veterinarian, health professional, sales professional or organization, and/or radio or television media (i.e., advertisement) or written direction (e.g., through written direction from, for example, a physician, veterinarian, or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" includes through words, pictures, symbols, and/or other visible descriptors. Such direction need not utilize the actual words used herein, but rather use of words, pictures, symbols, and the like conveying the same or similar meaning are contemplated within the scope of this invention.

The present diet formulations, and the various components within the formulations, may be administered in accordance with various levels as one of ordinary skill in the art will understand. Again, the formulation comprises moderate amounts of carbohydrate and fat in combination with higher amounts of protein. The specific dosage of the diet to be administered, as well as the duration of treatment, may be interdependent. The dosage and treatment regimen will also depend upon such factors as the specific diet used, the diet indication, the personal attributes of the animal (such as, for example, weight, age, gender and medical condition of the animal), compliance, with the treatment regimen, and the presence and severity of any side effects of the treatment. One of ordinary skill in the art will be able to select the specific diet formulation used based on these guidelines.

To illustrate, for a human, the formulation may comprise foods from the recommended food groups chosen to provide a level of protein that is at least about 40%, a level of carbohydrate that is about 30% and a level of fat that is no more than about 20% on a percent of calories basis.

As further illustration, for a companion animal, the diet may comprise, on a percent of calories basis, protein at a level of at least about 40%, carbohydrate at a level of equal to or less than about 35%, and fat at a level of equal to or less than about 32%. Even more preferably, the companion animal diet comprises, on a percent of calories basis, protein at a level of from about 40% to about 54%, carbohydrate at a level of from about 14% to about 35%, and fat at a level of from about 22% to about 32%. In a further preferred embodiment, the companion animal diet comprises, on a percent of calories basis, protein at a level of from about 44% to about 48%, carbohydrate at a level of from about 25% to about 29%, and fat at a level of from about 25% to about 29%. Alternatively or additionally, for a companion animal, the diet typically comprises, on a dry matter weight basis, protein at a level of at least about 40%, carbohydrate at a level of equal to or less than about 32%, and fat at a level of equal to or less than about 17%.

The companion animal formulation may optionally comprise a moist, semi-moist, or dry food. Suitable ingredients for the diet may include one or more vitamins, minerals, antioxidants, or other nutrients known to those of ordinary skill in the art. The food can be canned, as is most moist food, or can be provided as a kibble, for example wherein the vitamins, minerals, antioxidants, fiber, protein and fat, for example, are combined with a gelatinized starch matrix. To illustrate, the food can be formed by baking, extruded by use of a single- or twin-screw extruder, or formed by other means known to those of skill in the art of food manufacturing.

Carbohydrates for a diet formulation utilized under the methods of the present invention can be derived from a number of sources known to those of skill in the art such as, for example, corn, barley, sorghum, rice, wheat, oats, or mixtures thereof. The inventors particularly recommend the use of a low glycemic index grain carbohydrate source to achieve more optimum modulation of glucose metabolism.

Fats incorporated into a diet formulation as described by the method of the present invention can also be derived from a number of sources known to those of skill in the art such as, for example, poultry fat, pork fat, chicken fat, beef or other animal fats, vegetable oils (such as, for example, sunflower or corn oil), fish oil, fish meal, or mixtures thereof.

Protein sources for the method of the present invention can be derived from sources known to those of skill in the art such as, for example, chicken, beef, vegetable (such as, for example, corn gluten meal, soy), pork, lamb, turkey, fish, or mixtures thereof.

Figure 9:
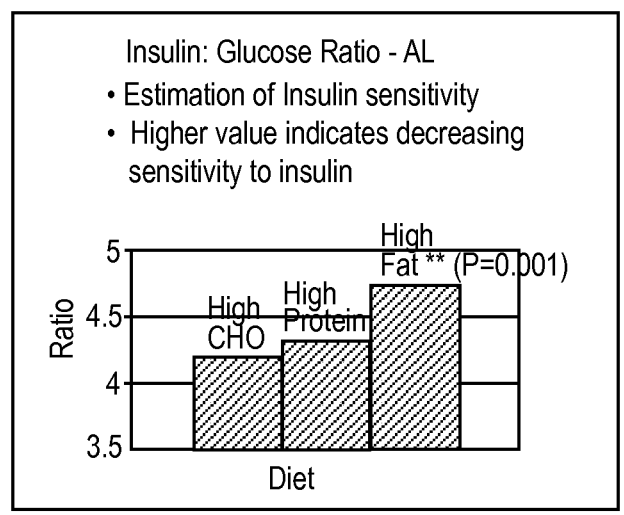
FIG. 9 is a bar graph illustrating the average insulin: glucose ratio in blood samples taken from cats following the feeding studies. The numeric ratio is indicated on the Y axis and the type of diet (Diet 1—high protein, Diet 2—high fat, Diet 3—high carbohydrate) is indicated on the X axis.

As indicated by the results shown in FIG. 1 through FIG. 8, the high protein diet designated as Diet 1, while containing approximately 27% carbohydrate (on a percent of calories basis), provides lower glucose and insulin concentrations than either Diet 2 (high fat) or Diet 3 (high carbohydrate). More importantly, as shown in FIG. 9, the high protein. diet, while providing a moderate amount of carbohydrate, actually provides comparable insulin: glucose ratio with the high carbohydrate diet and a lower insulin: glucose ratio than the high fat diet. Since the insulin: glucose ratio is an indicator of the body's sensitivity to insulin, with a higher value indicating a decreased sensitivity to insulin, the results shown in FIG. 9 demonstrate that feeding diets that provide higher fat levels can increase the insulin: glucose ratio, a measure of the development of insulin resistance. Feeding a diet higher in protein, with moderate carbohydrate and decreased fat levels, however, provides a more acceptable insulin: glucose ratio and is less likely to promote the development of insulin resistance.

Since insulin resistance correlates with the development of certain diseases normally associated with aging and decreased longevity (Facchini et al., "Insulin Resistance as a Predictor of Age-Related Diseases," *J. Clin. Endocrinology & Metabolism* Vol. 86, 3574 (2001)) diets that promote insulin sensitivity and decrease insulin resistance provide a means for preventing much age-associated disease and for prolonging life span and improving the quality of life for a human or other animal. Ramsey et at., "Dietary restriction and aging in rhesus monkeys: the University of Wisconsin study," *Exp. Geronotology* Vol. 35, 1131 (2000), have shown that insulin sensitivity is higher in animals maintained on a regimen of dietary restriction, which has been linked to increased lifespan in rodents, primates, and in canines (see, for example, Kealy et at, "Effects of diet restriction on life span and age-related changes in dogs," *JAVMA*, Vol, 220, 1315 (2002); Lane et at., "Calorie restriction in nonhuman primates: implications for age-related disease risk," *J. Anti-aging Med.*, Vol. 1, 315 (1998), The method of the present invention therefore provides a means for individuals who are either unable or unwilling to prevent age-associated abnormalities of glucose metabolism through diet restriction or caloric restriction for themselves or companion animals.

The invention can be described further by means of the following non-limiting Examples.

EXAMPLES

Diets designated as Diet 1 (approximately 46% protein, 26% fat, and 27% carbohydrate, all on a percent of calories basis), Diet 2 (approximately 26% protein, 47% fat, and 26% carbohydrate, all on a percent of calories basis), and Diet 3 (approximately 25% protein, 27% fat, and 47% carbohydrate, all on a percent of calories basis), are shown in Table 1.

TABLE 1

| Diet | Fat | Ash | CF | Pro | Moist | Calories/100 g |
| --- | --- | --- | --- | --- | --- | --- |
| 1 | 10.83 | 7.20 | 1.32 | 46.66 | 6.51 | 376.04 |
| 2 | 23.26 | 5.20 | 1.27 | 31.32 | 6.83 | 450.31 |
| 3 | 11.23 | 4.45 | 1.38 | 26.48 | 7.38 | 388.61 |

Twenty-four (24) healthy, sprayed/neutered cats (12 female, 12 male) with average body weight of 5.0 kg were chosen. All cats were determined to be non-obese based on body condition score. Cats were blocked into three (3) groups based on gender, body condition score, and plasma glucose and insulin concentrations during a simplified glucose tolerance test (GTT).

Cats were fed a standard diet (similar in composition to many commercially available feline diets, such as SCIENCE DIET® or IAMS®} for four weeks. After baseline testing, cats were randomly assigned to be provided with one of three test diets (Diets 1-3, as described above). Meal response and ad libitum feeding tests were performed prior to and after four weeks of feeding of tests diets. Following either meal response or ad libitum testing, plasma glucose and insulin concentrations were measured.

For ad libitum testing, cats were given free access to food over a 12-hour period. Caloric intake was recorded, and blood samples were collected via jugular catheter at 0, 1, 2, 3, 4, 6, 8, 10 and 12 hours. This test was performed to investigate glucose/Insulin response in the feeding pattern adopted by cats when food is plentiful and provided without specific limitation.

For the meal response feeding test, food was restricted to 50 Kcal/kg BW for 24 hours, and food was withheld for twelve (12) hours before the test. On average, during a period of 0.5 hour, cats in the meal response test ate 90% or more of the amount of food consumed during 12 hours when food was provided ad libitum. Caloric intake was recorded and blood samples were collected via jugular catheter at 0, 1, 2, 3, 4, 6, 8, 10, 12, 15, 18, and 24 hours, Results from both, meal response and ad libitum testing are shown in FIGS. 1 through 9.

All documents cited herein are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for preventing age associated abnormalities in a dog comprising administering to the dog a diet formulation comprising from about 14% to about 35% carbohydrate, at least about 40% protein, and equal to or less than about 32% fat, all on a percent of calories basis.

2. The method of claim 1 wherein the diet formulation comprises at least about 40% protein, on a dry matter weight basis.

3. The method of claim 2 wherein the diet formulation comprises equal to or less than about 17% fat on a dry matter weight basis.

4. The method of claim 3 wherein the diet formulation comprises equal to or less than about 32% carbohydrate on a dry matter weight basis.

5. The method of claim 1 wherein the diet formulation comprises equal to or less than about 32% carbohydrate on a dry matter weight basis.

6. The method of claim 1 wherein the diet formulation comprises from about 40% to about 54% protein, and from about 22% to about 32% fat, on a percent of calories basis.

7. The method of claim 1 wherein the diet formulation comprises from about 44% to about 48% protein, on a percent of calories basis.

8. The method of claim 1 wherein the diet formulation comprises from about 25% to about 29% carbohydrate, on a percent of calories basis.

9. The method of claim 1 wherein the diet formulation comprises about 25% to about 29% fat, on a percent of calories basis.

10. The method of claim 1 wherein the carbohydrate is a low glycemic index grain carbohydrate.

11. The method of claim 1 wherein the dog has symptoms of insulin resistance, diabetes, pre-diabetes, hypertriglyceridemia, hyperlipidemia, or combinations thereof.

12. The method of claim 11 wherein the symptoms were not corrected by caloric restriction.

13. The method of claim 1 wherein the diet formulation is administered ad libitum.

14. The method of claim 1 wherein the diet formulation is administered in measured portions.

15. The method of claim 14 wherein the diet formulation is administered once daily.

16. The method of claim 14 wherein the diet formulation is administered twice daily.

17. The method of claim 14 wherein the diet formulation is administered three times daily.

* * * * *